United States Patent [19]

Ueyama et al.

[11] Patent Number: 4,965,133
[45] Date of Patent: Oct. 23, 1990

[54] MODIFYING AGENT FOR CONDUCTIVE SUBSTRATE

[75] Inventors: Satoshi Ueyama; Satoru Isoda, both of Hyogo, Japan

[73] Assignee: Kozo Iizuka, Director General, Agency of Industrial Science and Technology, Tokyo, Japan

[21] Appl. No.: 444,946

[22] Filed: Dec. 4, 1989

Related U.S. Application Data

[62] Division of Ser. No. 243,600, Sep. 13, 1988.

[30] Foreign Application Priority Data

Dec. 24, 1987 [JP] Japan ................................ 62-325525

[51] Int. Cl.$^5$ .............................................. B32B 9/04
[52] U.S. Cl. .................................... 428/411.1; 427/58; 427/430.1; 844/345
[58] Field of Search ............... 427/58, 430.1; 544/345; 428/411.1

[56] References Cited

U.S. PATENT DOCUMENTS 4,584,235  4/1986  Roberts et al. .................... 427/58 X Primary Examiner—Michael Lusignan
Attorney, Agent, or Firm—Bernard, Rothwell & Brown

[57] ABSTRACT

A modifying agent for a conductive substrate comprises a flavin derivative. A flavin-modified electrode obtained through modification by the modifying agent is capable of reducing an electron transfer protein having a standard oxidation-reduction potential higher than, or on the positive side of, the standard oxidation-reduction potential of the flavin derivative but is incapable of oxidizing the electron transfer protein, and is therefor capable of controlling electron transport so that the electron transport takes place in only one direction. With this characteristic feature, the modified electrode is applicable to functional devices such as diodes, transistors and optical switch devices.

6 Claims, 3 Drawing Sheets

E: CYCLIC VOLT-AMOGRAM WITHOUT ADDITION OF CYTOCHROME·C

F: CYCLIC VOLT-AMOGRAM WITH ADDITION OF CYTOCHROME·C

MODIFYING AGENT FOR CONDUCTIVE SUBSTRATE

This is a division of application Ser. No. 243,600, filed Sept. 13, 1988.

BACKGROUND OF THE INVENTION

1. Field of the Invention

The present invention relates to a modifying agent for a conductive substrate for use in producing a chemically modified electrode.

2. Prior Art

As modifying agents for producing chemically modified electrodes used for efficient reduction of an electron transfer protein, there have been known promotors such as 4,4'-bipyridyl, as described in J. Am. Chem. Soc., 101, p4461 (1979), and, also, mediators such as ferrocene derivatives, as described in J. Am. Chem. Soc., 105, p181 (1983).

FIG. 1(a) shows the structural formula of 4,4'-bipyridyl, and FIG. 1(b) shows the structural formula of a ferrocene derivative.

The operation of the conventional modified electrodes will now be explained. FIG. 2 shows a cyclic voltamogram obtained by immersion of a modified electrode, obtained by modifying gold by the promotor shown in FIG. 1(a), in an aqueous solution of cytochrome c, which is one of electron transfer proteins. In FIG. 2, peaks corresponding to reduction and oxidation of cytochrome c are observed, showing that cytochrome c can be oxidized and reduced by use of the electrode. Similarly, it is possible to oxidize and reduce cytochrome c by use of a modified electrode obtained by modifying platinum by the mediator shown in FIG. 1(b). In FIG. 2, the ordinate indicates current ($\mu$A) and the abscissa indicates voltage (mV).

With the conventional promotor-modified electrode constructed as described above, bidirectional electron transfer takes place between cytochrome c and the electrode and, therefore, it is impossible to control the flow of electrons to only one direction, from the electrode to cytochrome c. In the case of the mediator-modified electrode, the method of modification is complicated. Besides, where the difference in oxidation-reduction potential between the modifying agent and the electron transfer protein is small, as in the case of a combination of ferrocene and cytochrome c, bidirectional electron transfer takes place similarly to the above case of the promotor-modified electrode, and it is therefore impossible to control the direction of electron flow.

It is possible to achieve the desired control of the direction of electron flow between a modified electrode and an electron transfer protein such as cytochrome c, by using a flavin derivative having a standard oxidation-reduction potential lower than, or on the negative side of, the standard oxidation-reduction potential of the electron transfer protein to produce the modified electrode. However, it has been difficult to modify a conductive substrate by commercially available riboflavin or lumifravin.

SUMMARY OF THE INVENTION

An object of the present invention, attained in order to solve the above-mentioned problems, is to provide a modifying agent for a conductive substrate which is capable of stably modifying the conductive substrate so as to enable efficient reduction of an electron transfer protein, such as cytochrome c, having a standard oxidation-reduction potential higher than, or on the positive side of, the standard oxidation-reduction potential of a flavin derivative.

The modifying agent for a conductive substrate according to the present invention comprises a flavin derivative represented by the general formula:

$$\text{[structural formula with } CH_2(CHOR1)_3CH_2OR1 \text{, R3, R4, NR2]}$$

wherein R1 represents a hydrogen atom or an acyl group, R2 and R3 each represent a hydrogen atom or a lower alkyl group having one to four carbon atoms, and R4 represents a thiocyanato group or a mercapto group.

Other objects and advantages of the present invention will become more apparent from the following detailed description of preferred embodiments, taken in conjunction with the accompanying drawings.

PREFERRED EMBODIMENT OF THE INVENTION

Figure 1A:
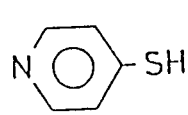
FIGS. 1(a) and 1(b) show respectively the structural formulas of conventional modifying agents.
Figure 1B:
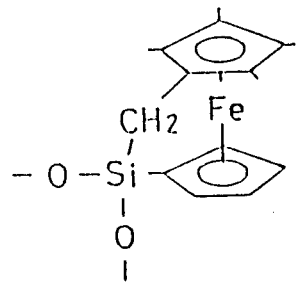
Figure 2:
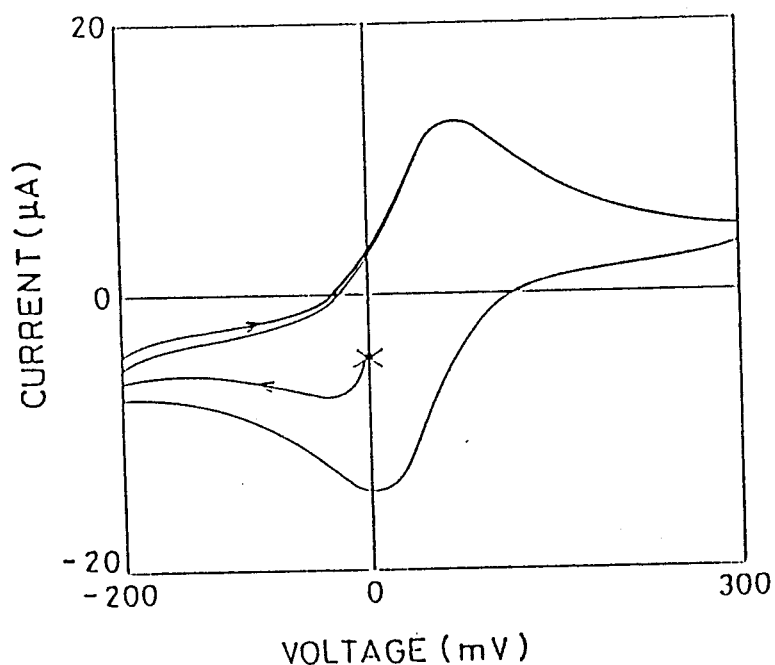
FIG. 2 shows a cyclic voltamogram based on the use of a conventional modified electrode.

Of the novel flavin derivatives represented by the general formula:

$$\text{[structural formula with } CH_2(CHOR1)_3CH_2OR1 \text{, R3, R4, NR2]}$$

wherein R1 represents a hydrogen atom or an acyl group, R2 and R3 each represent a hydrogen atom or a lower alkyl group having one to four carbon atoms, and R4 represents a thiocyanato group or a mercapto group, as the modifying agent for a conductive substrate according to the present invention, those in which R4 is a thiocyanato group, namely, 6-thiocyanatoflavin derivatives can be prepared by reacting a 6-aminoflavin derivative, known in the literature [for instance, Biochemistry, 19, p2537 (1980)], with 1.5 to 5 times as much sodium nitrite as the 6-aminoflavin derivative by mole in a 15 to 40% aqueous sulfuric or hydrochloric acid solution to form a 6-diazoflavin derivative and then, without isolation, reacting the 6-diazoflavin derivative with potassium thiocyanate.

The objective 6-mercaptoflavin derivatives, represented by the above general formula in which R4 is a mercapto group, can be prepared by reacting a 6-thiocyanatoflavin derivative with a reducing agent (for instance, sodium hydrosulfite, sodium boron hydride or dithiothreitol) in an aqueous solution or by reacting the 6-thiocyanatoflavin derivative with EDTA under irradiation with light. Both the 6-thiocyanatoflavin derivatives and the 6-mercaptoflavin derivatives can be isolated by the usual recrystallization process or purification processes employing molecular sieves, silica gel columns, resin columns or the like.

The above-mentioned flavin derivatives can be used to modify a conductive substrate, as follows. The flavin derivative prepared as described above is dissolved in water or a buffer solution, for instance, in a concentration of 0.1 to 100 mg/l. The conductive substrate constituted of, for example, a metal such as gold, silver, platinum, etc. cleaned with water, a concentrated acid, an organic solvent or the like, a metallic oxide such as tin oxide, or a semiconductor such as silicon, carbon, etc. is immersed in the flavin derivative solution for a period of time ranging from 0.1 sec to 1 hour, whereby a flavin-modified electrode can be obtained.

The present invention will now be described more in detail below while referring to the following nonlimitative Examples.

Example 1

Synthesis of
6-thiocyanato-2',3',4',5'-tetraacetylriboflavin

In a 0° C. mixture of 10 ml of concentrated sulfuric acid and 30 ml of iced water, 1.00 g (1.79 mmol) of 6-amino-2',3',4',5'-tetraacetylriboflavin was suspended. After adding 19.05 mg (2.68 mmol) of 97% sodium nitrite to the suspension at 0° C., the resultant mixture was agitated at that temperature for 15 min. Then, 19.55 mg of urea was added to the mixture at 0° C. to decompose excess sodium nitrite, followed by agitation for another 15 min. After sufficient decomposition, 0.85 ml of a saturated aqueous solution of potassium thiocyanate was added to the mixture at 0° C., and the resultant mixture was agitated until evolution of nitrogen gas stopped (about 30 min.).

By using 30 ml of 25% aqueous ammonia at a temperature of 15° C., the pH of the reaction mixture was made finally to be 2. The reaction mixture was extracted three times with 50 ml each of chloroform (150 ml, in total), and the gathered chloroform solution was dried over anhydrous sodium sulfate. After the solvent was distilled off under a reduced pressure, the residue was served to a silica gel column (eluent: acetone/benzene=1:5), and the objective fraction was gathered, from which the solvent was distilled off under a reduced pressure. The residue thus obtained was subjected to recrystallization from a chloroform-benzene mixture to give 367 mg of yellow crystals of the objective 6-thiocyanato-2',3',4',5'-tetraacetylriboflavin. Yield 34.1%.

The compound thus obtained was identified as the objective compound, by the following measurements.
Melting point: 138–142° C.
Elemental analysis (%):
  Calcd.: C, 51.92; H, 4.52; N, 11.62.
  Found : C, 51.65; H, 4.52; N, 11.52.
IR absorption spectrum (KBr, cm$^{-1}$): 3470, 2150, 1740, 1580, 1535, 1215.
NMR spectrum (CDClhd 3, δ ppm): 1.82, 2.09, 2.21, 2.66, 2.76 (each 3H, s), 4.25, 4.44 (each 1H, d), 5.41 (4H, broad), 5.60 (1H, broad), 7.77, 8.61 (each 1H, sharp).

Modification of gold-evaporated electrode by thiocyanatotetraacetylriboflavin

Figure 4:
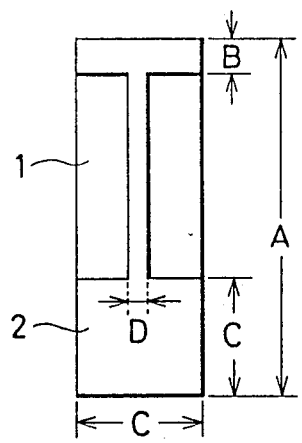
FIG. 4 shows a front view of a gold electrode as a conductive substrate.

As shown in FIG. 4, a front view of a gold electrode, a gold-evaporated glass substrate was washed with distilled water and then immersed in concentrated nitric acid for 10 min to obtain a cleaned gold electrode. Separately, 6-thiocyanato-2',3',4',5'-tetraacetyriboflavin was dissolved in a phosphoric acid buffer solution (pH 7.0, 20 mM) in a concentration of 10 mg/l. The cleaned gold electrode was immersed in the thus obtained aqueous solution for 10 min, and was washed with water to obtain a stable flavin-modified electrode.

In the figure, numeral 1 denotes a glass substrate, and numeral 2 denotes an evaporated gold film, while the dimensions A, B, C and D are respectively 50 mm, 3 mm, 10 mm and 2 mm.

Stability test of modified electrode by cyclic voltammetry

Figure 5:
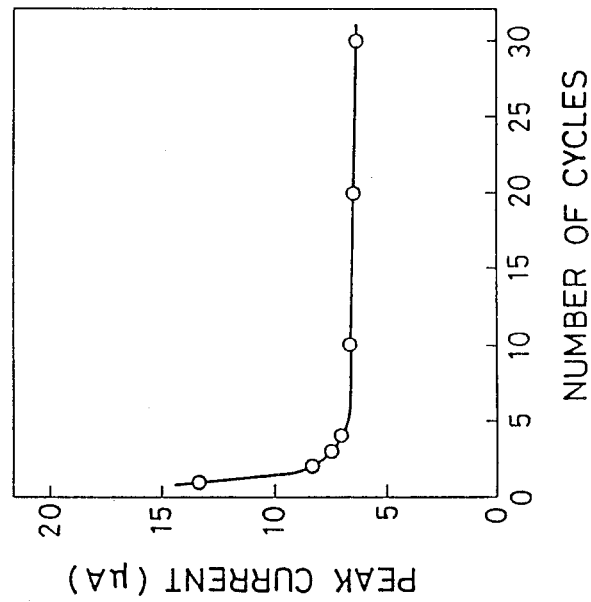
FIG. 5 is a characteristic diagram showing variations in the height ($\mu$A) of the reduction peak with the number of cycles for the modified electrode obtained by use of the modifying agent for a conductive substrate according to one embodiment of the present invention.

In a phosphoric acid buffer solution (pH 7.0, 20 mM), sodium perchlorate was dissolved in a concentration of 100 mM, followed by deoxidation by passing an argon gas. With the resultant solution as a electrolytic solution, the modified electrode obtained above was served to cyclic voltammetry (0 to −600 mV vs. Ag/AgCl, sweep rate 50 mV/s). FIG. 5 is a characteristic diagram showing the variations in the reduction peak height with the number of cycles. The diagram shows that after three cycles, the reduction peak height is little varied, which indicates stable adsorption of 6-thiocyanato-2',3',4',5'-tetraacetylriboflavin on the gold surface. In the diagram, the ordinate indicates peak current (μA) and the abscissa indicates the number of cycles.

Reduction of cytochrome c

Figure 3:
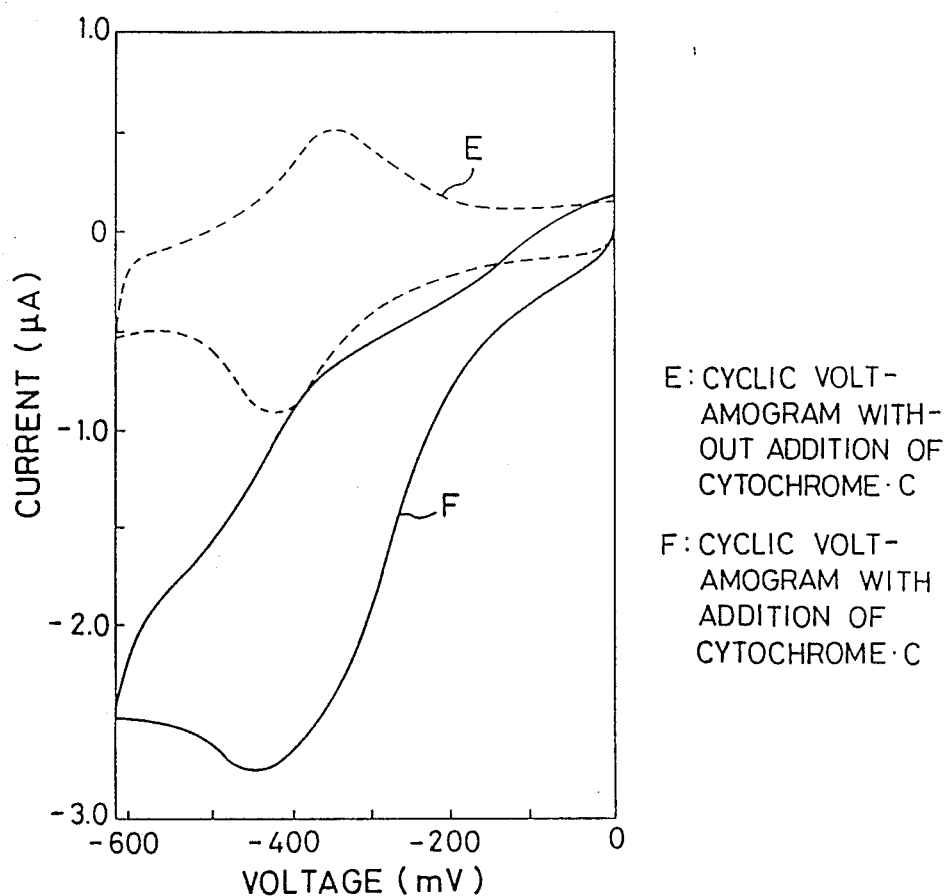
FIG. 3 shows a cyclic voltamogram based on the use of a modified electrode obtained by use of a modifying agent for a conductive substrate according to one embodiment of the present invention.

Cytochrome c was dissolved in the above-mentioned electrolytic solution in a concentration of 330 μM, and cyclic voltammetry was carried out by using the above-mentioned flavin-modified electrode in the solution thus obtained. The result is shown as a cyclic voltammogram in FIG. 3, in comparison with that obtained in the electrolytic solution not containing cytochrome c.

No oxidation peak is recognized in the cyclic voltamogram thus obtained, while a large flow of reduction current exists. This indicates that by use of the modified electrode, it is possible to reduce cytochrome c but it is impossible to oxidize cytochrome c. Namely, use of the modified electrode makes it possible to cause electron transfer in only one direction from the electrode to cytochrome c.

In the figure, curve E is the cyclic voltammogram obtained without addition of cytochrome c to the electrolytic solution, while curve F is the cyclic voltarmogram obtained with addition of cytochrome c to the electrolytic solution. The ordinate indicates current (μA) and the absciss indicates voltage (mV) relative to an Ag/AgCl electrode.

Example 2

In a 0.05 M potassium dihydrogenphosphate-disodium phosphate buffer solution (pH 7.0), the 6-thiocyanato-2',3',4',5'-tetraacetylriboflavin obtained in Example 1 was dissolved in a concentration of $5.10 \times 10^{-5}$ M. To the thus prepared solution, disodium EDTA was added as a stabilizer in such an amount as to attain a concentration of $1.0 \times 10^{-4}$ M, thereby obtaining a sample solution.

Figure 6:
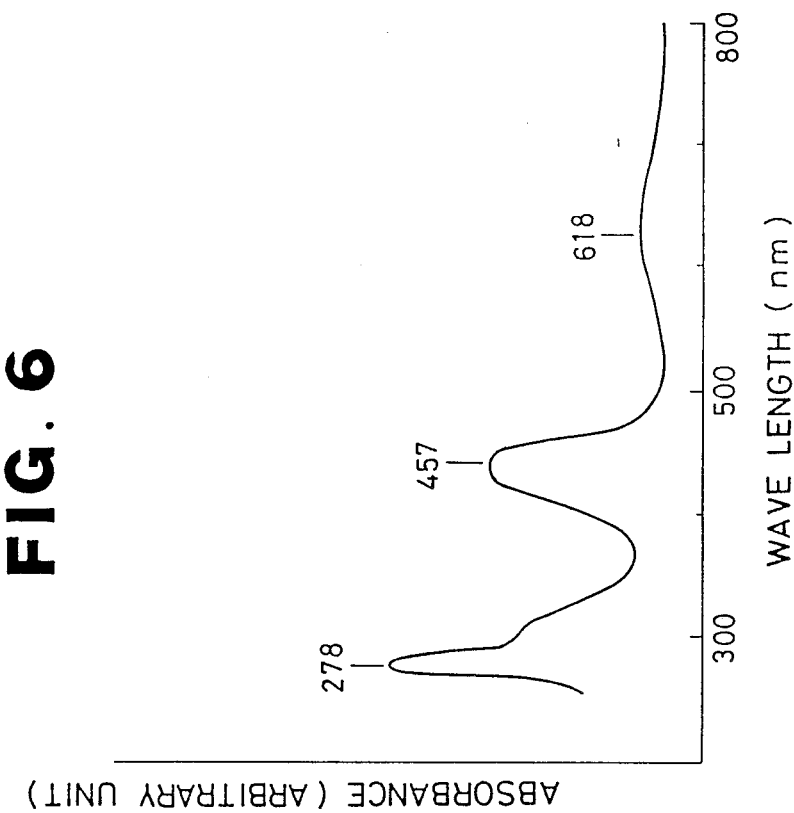
FIG. 6 shows a visible and ultraviolet absorption spectrum of a modifying agent for a conductive substrate according to another embodiment of the present invention.

To the sample solution, dithiothreitol was added in such an amount as to attain a concentration of $8.0 \times 10^{-4}$ M. The resultant mixture was agitated for 2 hours at room temperature to form the objective 6-mercapto-2',3',4',5'-tetraacetyriboflavin. The visible and ultraviolet absorption spectrum of the product is shown in FIG. 6.

The thus synthesized 6-mercapto-2',3',4',5'-tetraacetylriboflavin is also usable as a modifying agent for a conductive substrate, in the same manner as in Example 1, to produce the same effect as in Example 1.

Example 3

A sample solution was prepared in the same manner as in Example 2 except that disodium EDTA was not added. To the sample solution, sodium hydrosulfite was added in such an amount as to attain a concentration of $8.0 \times 10^{-4}$ M in a nitrogen atmosphere, and the resultant mixture was agitated for 1 hour and 30 min at room temperature. The ultraviolet absorption spectrum of the thus formed 6-mercapto-2',3',4',5'-tetraacetylriboflavin agreed with that obtained in Example 2. The thus synthesized 6 mercapto-2',3',4',5'-tetraacetylriboflavin is also usable as a modifying agent for a conductive substrate in the same manner as in Example 1, to produce the same effect as in Example 1.

Although the descriptions of the Examples above have been made referring to the use of 6 thiocyanato-2',3',4',5'-tetraacetylriboflavin and of 6-mercapto 2',3',4',5'-tetraacetylriboflavin, other flavin derivatives in which a mercapto group or a thiocyanato group has been introduced are also capable of stably modifying a conductive substrate to produce the same effect as in the Examples.

Besides, though the descriptions of the Examples above have been made referring to the use of cytochrome c as the electron transfer protein, the same effect as above is obtainable also in the case of using other electron transfer protein such as rubredoxin, etc.

As has been stated above, according to the present invention, a modifying agent for a conductive substrate which comprises a flavin derivative represented by the general formula:

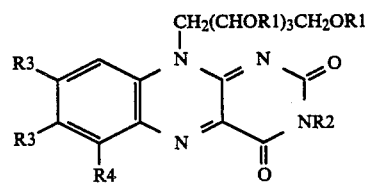

wherein R1 represents a hydrogen atom or an acyl group, R2 and R3 each represent a hydrogen atom or a lower alkyl having one to four carbon atoms, and R4 represents a thiocyanato group or a mercapto group, is used, whereby it is possible to stably modify the conductive substrate so as to enable efficient reduction of an electron transfer protein having a standard oxidation-reduction potential higher than, or on the positive side of, the standard oxidation-reduction potential of the flavin derivative. The modified electrode obtained by the use of the modifying agent for a conductive substrate according to the invention is applicable to functional devices such as diodes, transistors, optical switch devices, etc.

What is claimed is:

1. A conductive substrate, at least a portion of which has been chemically modified by being immersed in a solution containing an effective amount of a flavin derivative represented by the formula:

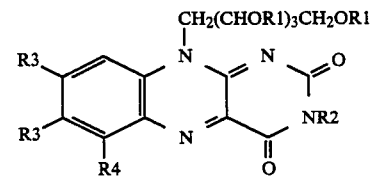

wherein R1 represents a hydrogen atom or an acyl group, R2 and R3 each represent a hydrogen atom or a lower alky group having one to four carbon atoms, and R4 represents a thiocyanato group or a mercapto group.

2. The conductive substrate of claim 1, wherein said flavin derivative comprises a 6- thiocyanatoflavin derivative.

3. The conductive substrate of claim 1, wherein said flavin derivative comprises a 6- mercaptoflavin derivative.

4. A process for preparing a chemically modified conductive substrate comprising dissolving in a solution an effective amount of a flavin derivative of the formula:

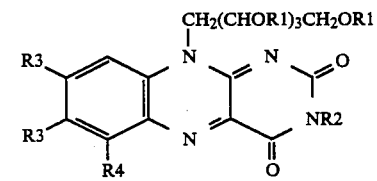

wherein R1 represents a hydrogen atom or an acyl group, R2 and R3 each represent a hydrogen atom or a lower alkyl group having one to four carbon atoms, and R4 represents a thiocyanato group or a mercapto group and immersing at least a portion of a conductive substrate in said solution.

5. The process of claim 4, wherein said flavin derivative comprises a 6-thiocyanatoflavin derivative.

6. The process of claim 4, wherein said flavin derivative comprises a 6-mercaptoflavin derivative.

* * * * *

UNITED STATES PATENT AND TRADEMARK OFFICE
CERTIFICATE OF CORRECTION

PATENT NO. : 4,965,133

DATED : October 23, 1990

INVENTOR(S) : Satoshi Ueyama

It is certified that error appears in the above-identified patent and that said Letters Patent is hereby corrected as shown below:

Column 4, line 11, "CDClhd3" should be --CDCl$_3$--;

Column 5, line 4, "absciss" should be --abscissa--;
line 9, "dihydrogenphosphate-disc-" should be --dihydrogenphosphate-diso- --;
line 23, "tetraacetyriboflavin" should be --tetraacetylriboflavin--;
line 44, "6 mercapto-" should be --6-mercapto- --.

Signed and Sealed this

Twenty-ninth Day of September, 1992

Attest:

DOUGLAS B. COMER

*Attesting Officer*   *Acting Commissioner of Patents and Trademarks*